(12) United States Patent
Lim et al.

(10) Patent No.: US 8,835,663 B2
(45) Date of Patent: Sep. 16, 2014

(54) LUBRICITY IMPROVER

(75) Inventors: Young-Kwan Lim, Chungcheongnam-do (KR); Joung Min Lee, Gyeonggi-do (KR); Choong-Sub Jung, Gyeonggi-do (KR); Jong-Ryeol Kim, Gyeonggi-do (KR); Eui Soon Yim, Chungcheongbuk-do (KR)

(73) Assignee: Korea Institute of Petroleum Management, Seongnam-Si, Gyeonggi-Do (KR)

( * ) Notice: Subject to any disclaimer, the term of this patent is extended or adjusted under 35 U.S.C. 154(b) by 266 days.

(21) Appl. No.: 13/548,501

(22) Filed: Jul. 13, 2012

(65) Prior Publication Data

US 2013/0053590 A1 Feb. 28, 2013

(30) Foreign Application Priority Data

Aug. 22, 2011 (KR) .................. 10-2011-0083620

(51) Int. Cl.
| | | |
|---|---|---|
| *C07C 51/00* | (2006.01) | |
| *C07C 59/00* | (2006.01) | |
| *C10M 129/02* | (2006.01) | |
| *C10L 1/19* | (2006.01) | |
| *C07C 69/708* | (2006.01) | |

(52) U.S. Cl.
CPC .......... *C07C 69/708* (2013.01); *C10M 129/02* (2013.01); *C10L 2270/026* (2013.01); *C10N 2230/64* (2013.01); *C10M 2207/04* (2013.01); *C10L 1/19* (2013.01); *C10N 2230/06* (2013.01)
USPC ................... 554/153; 554/150; 554/213

(58) Field of Classification Search
CPC .................................. C07C 69/00
USPC ............................. 554/150, 153, 213
See application file for complete search history.

(56) References Cited

U.S. PATENT DOCUMENTS

| | | | |
|---|---|---|---|
| 3,976,623 A | 8/1976 | Vollkommer | |
| 4,031,158 A | 6/1977 | Isa et al. | |
| 4,609,376 A | 9/1986 | Craig et al. | |
| 6,511,520 B1 | 1/2003 | Eber et al. | |

FOREIGN PATENT DOCUMENTS

| | | |
|---|---|---|
| EP | 0605857 A1 | 7/1994 |
| EP | 0635558 A1 | 1/1995 |
| JP | 6-298692 | 10/1994 |
| KR | 1999-0043777 | 6/1999 |
| KR | 10-2005-0052460 | 6/2005 |

*Primary Examiner* — Deborah D Carr
(74) *Attorney, Agent, or Firm* — Finnegan, Henderson, Farabow, Garrett & Dunner, L.L.P.

(57) ABSTRACT

Provided is a lubricity improver capable of improving lubricity and storage stability due to anti-oxidation, the lubricity improver containing a saturated fatty acid methyl ester derivative including at least one 1,2-dimethoxy ethylene structural unit represented by Chemical Formula a below, obtained by converting a double bond (olefin) of biodiesel, which is used as a lubricity improver of fuel, that is, the existing fatty acid methyl ester (FAME), into a dimethoxy group.

[Chemical Formula a]

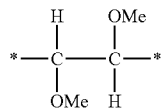

9 Claims, No Drawings

LUBRICITY IMPROVER

CROSS-REFERENCE TO RELATED APPLICATIONS

This application claims priority under 35 U.S.C. §119 to Korean Patent Application No. 10-2011-0083620, filed on Aug. 22, 2011, in the Korean Intellectual Property Office, the disclosure of which is incorporated herein by reference in its entirety.

TECHNICAL FIELD

The following disclosure relates to a lubricity improver capable of improving lubricity and storage stability due to anti-oxidation, and more particularly to lubricity improver containing a saturated fatty acid methyl ester derivative including at least one 1,2-dimethoxy ethylene structural unit obtained by converting a double bond (olefin) of biodiesel, which is used as a lubricity improver of fuel, that is, the existing fatty acid methyl ester (FAME), into a dimethoxy group.

BACKGROUND

Lubricity reduces the friction that is inevitably generated between two faces that relatively move at the time of transfer of force or change of direction due to mechanical mechanism. In order to improve this lubricity, a lubricity improver is used at most facilities where the mechanical mechanism occurs, and thus, the lifespan of a machine can be extended, resulting in increasing production activity. Meanwhile, since a high-pressure ignition type diesel engine as well as the machine requires lubricity of fuel, a lubricity improver is mixed in the fuel at a predetermined mixture ratio in order to secure lubricity of the fuel for diesel engine.

The lubricity improver may be largely classified into inorganic compounds, metals, and organic compounds. There are polymers, synthetic lubricant from metal oil, and the like. Recently, a vegetable lubricant has been increasingly used as an ecofriendly lubricant. In the vegetable lubricant, fatty acid methyl ester obtained from animal or vegetable oil has been known to have excellent lubricity.

U.S. Pat. No. 4,609,376 discloses, as a lubricity improving additive for alkanol fuel, ester of monovalent or polyvalent carboxylic acid and polyvalent alcohol (but, having at least two free hydroxy groups).

EP 0635,558 and EP 0605,857 disclose, as a lubricity improving additive of diesel fuel, vegetable oil such as rap seed oil, line seed oil, soya oil, canola oil, or sunflower oil, and ester of the vegetable oil.

Korean Patent Laid-Open Publication No. 10-2005-0052460 discloses, as a lubricity improving additive having improved low-temperature characteristics, a fatty acid composition having saturated fatty acid and unsaturated fatty acid, where fatty acids having different chain lengths are specifically distributed and specifically contained.

Korean Patent Laid-Open Publication No. 10-1999-0043777 discloses, as a lubricity improving additive, purified fatty acid, an ester compound obtained by reacting fatty acid and an alcohol compound, or a mixture thereof.

Meanwhile, the unsaturated fatty acid methyl ester containing olefin (double bond) is in a liquid phase while the saturated fatty acid methyl ester is mostly in a solid phase, and thus, the unsaturated fatty acid methyl ester has known to have excellent lubricity as compared with the saturated fatty acid methyl ester. However, when the unsaturated fatty acid methyl ester is stored for a long time, the olefin in the molecule is easily oxidized, which is converted into an epoxy group, a monol compound, or a diol compound, thereby changing physical property and increasing the acid value. Resultantly, this fatty acid methyl ester has poor storage stability, and since the acid value of the fatty acid methyl ester is increased at the time of storage thereof, it may corrode metals.

The corrosion of metals due to oxidation of the lubricity improver may accelerate mechanical friction and wear, resulting in deteriorating the condition of a machine.

That is, the lubricity improver needs to be in a uniform liquid state while being mixed in the fuel, needs to have excellent oxidation stability and good storage stability, and needs to reduce the friction and wear of two faces by providing excellent lubricity.

Although many studies on the existing fatty acid methyl ester type lubricity improver have been reported, there is no study that lubricity is improved and storage stability due to anti-oxidation is improved by substituting olefin in the fatty acid methyl ester with another functional group.

Therefore, in order to make up for the deficiencies of the existing fatty acid methyl ester type lubricity improver and improve the lubricity more effectively, a new type lubricity improver needs to be developed.

SUMMARY

Therefore, the present inventors found that, when using, as a lubricity improver, a saturated fatty acid methyl ester derivative including at least one 1,2-dimethoxy ethylene structural unit obtained by converting a double bond (olefin) of biodiesel, which is used as a lubricity improver of fuel, that is, the existing fatty acid methyl ester, into a dimethoxy group, lubricity can be improved and storage stability can be improved due to excellent oxidation stability, and then completed the present invention.

Therefore, an embodiment of the present invention is directed to providing a lubricity improver capable of improving lubricity and storage stability due to anti-oxidation.

Further, another embodiment of the present invention is directed to providing a lubricity improver containing a saturated fatty acid methyl ester derivative including at least one 1,2-dimethoxy ethylene structural unit.

Further, still another embodiment of the present invention is directed to providing a lubricity improver capable of, when a lubricant for reducing friction and wear of the existing mechanical equipment, a lubricity additive of light oil fuel, or fuel having bad lubricity (DME, GTL, CTL, or the like) in the renewable fuel as a replacement for limited petroleum resources is used in the existing diesel engine, reducing friction and wear to thereby maintain stability and performance of vehicles and extending the lifespan of machines and devices to thereby increase production activity.

Further, still another object of the present invention is directed to providing an ecofriendly lubricity improver using biodiesel obtained from animal and vegetable resources.

The present invention is directed to a lubricity improver capable of improving lubricity and storage stability due to anti-oxidation, and characterized by containing a saturated fatty acid methyl ester derivative including at least one 1,2-dimethoxy ethylene structural unit represented by Chemical Formula a below, obtained by converting a double bond (olefin) of biodiesel, which is used as a lubricity improver of fuel, that is, the existing fatty acid methyl ester (FAME), into a dimethoxy group.

[Chemical Formula a]

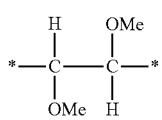

Biodiesel, which is fatty acid methyl ester (FAME), has been known to have an excellent effect in improvement of lubricity, since a methyl ester functional group is provided at a terminal portion thereof, to thereby enhance an adhesive strength between two moving faces, and a double bond also exhibits a polar function, to thereby influence an increase in adhesive strength. However, the biodiesel has a double bond (olefin) in a molecule, as compared with the existing petroleum diesel, and thus, when the biodiesel is stored for a long time while being exposed to air, it is easily oxidized into epoxide and alcohol compounds (monol and diol compounds). The oxidized fatty acid methyl ester may have changed fuel characteristics and may easily corrode metals due to the high acid value thereof.

The lubricity improver of the present invention contains a saturated fatty acid methyl ester derivative including at least one 1,2-dimethoxy ethylene structural unit obtained by converting a double bond (olefin) of biodiesel, which is used as a lubricity improver of fuel, that is, the existing fatty acid methyl ester, into a dimethoxy group, and improves the lubricity and improves storage stability due to excellent oxidation stability. In addition, when a lubricant for reducing friction and wear of the existing mechanical equipment, a lubricity additive of light oil fuel, or fuel having bad lubricity (DME, GTL, CTL, or the like) in the renewable fuel as a replacement for limited petroleum resources is used in the existing diesel engine, together with the lubricity improver of the present invention, the friction and wear can be reduced to thereby maintain stability and performance of vehicles and the lifespan of a machine and equipment can be extended to thereby increase production activity. In addition, the lubricity improver of the present invention is ecofriendly since it uses biodiesel obtained from animal and vegetable resources.

The lubricity improver according to the present invention includes a methoxylated fatty acid methyl ester derivative represented by Chemical Formula 1 below.

[Chemical Formula 1]

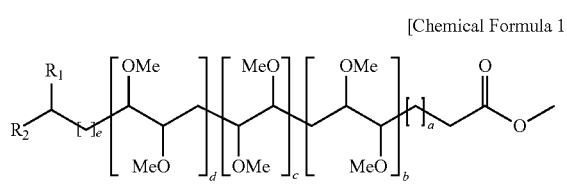

[Wherein Chemical Formula 1, $R_1$ and $R_2$ each are independently hydrogen or

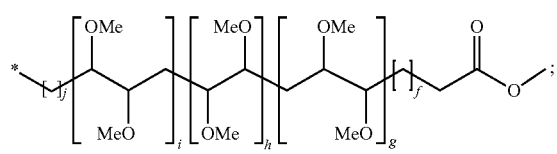

a, e, f, and j each are independently an integer of 1 to 10, and b, c, d, g, h, and i each are independently an integer of 0 to 5, provided that b+c+d and g+h+I each are independently an integer of 1 or greater.]

The methoxylated fatty acid methyl ester derivative of Chemical Formula 1 above is prepared by including: 1) preparing a hydroxylated fatty acid methyl ester derivative of Chemical Formula 3 by hydroxylating biodiesel of Chemical Formula 2 below including at least one double bond; and 2) preparing the methoxylated fatty acid derivative of Chemical Formula 1 by reacting the hydroxylated fatty acid methyl ester derivative of Chemical Formula 3 with halomethane in the presence of a base.

[Chemical Formula 2]

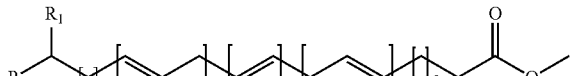

[Chemical Formula 3]

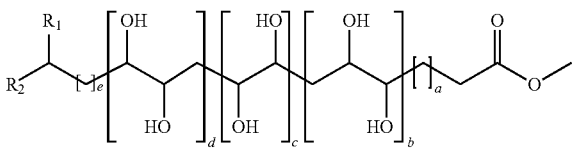

[In Chemical Formulas 2 and 3, $R_1$, $R_2$, a, b, c, d, and e have the same meanings as those defined in Chemical Formula 1 above.]

In Stage 1) above, the hydroxylating is carried out in the presence of an $OsO_4$ catalyst and 4-methylmorpholine N-oxide or t-butyl hydroperoxide, and in Stage 2) above, the base is selected from NaH, KH, KOt-Bu, NaOBu, and $NaNH_2$.

In addition, the biodiesel of Chemical Formula 2 above may be synthesized by esterification-reacting animal or vegetable oil selected from fat, pig fat, chicken fat, fish oil, soybean oil, olive oil, rapeseed oil, palm oil, perilla oil, sesame oil, sunflower oil, grape seed oil, red pepper seed oil, jatropha, cottonseed oil, and waste edible-oil, and alcohol. A synthesizing method of the biodiesel is a known technology, and thus detailed descriptions thereof will be skipped.

In addition, the lubricity improver according to the present invention includes a methoxylated fatty acid methyl ester derivative represented by Chemical Formula 4 below.

[Chemical Formula 4]

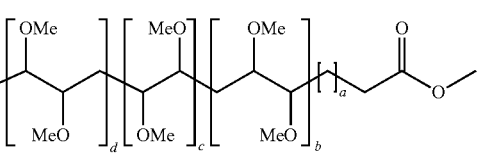

[In Chemical Formulas 4, a, b, c, d, and e have the same meanings as those defined in Chemical Formula 1 above.]

More specifically, the lubricity improver according to the present invention includes a methoxylated fatty acid methyl ester derivative selected from below:

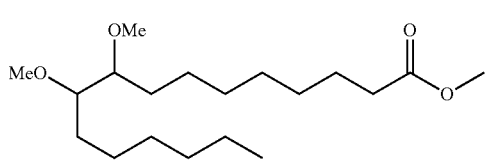

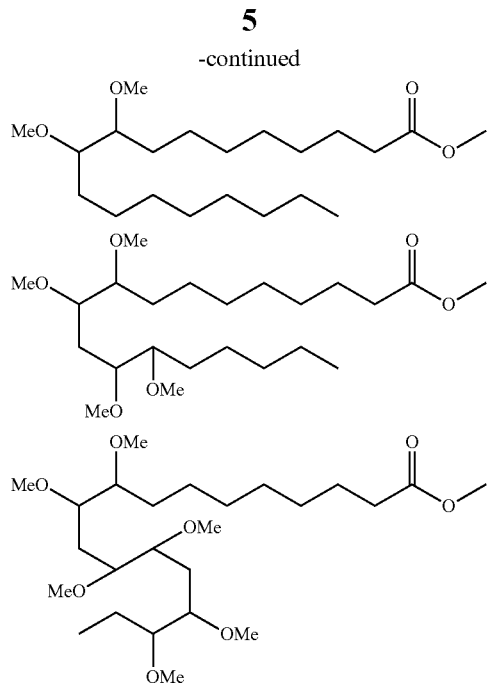

The lubricity improver according to the present invention may be used in order to improve lubricity of liquid type fuel such as, gasoline, kerosene, light oil, and alkanol fuels. The lubricity improver is mixed in 0.000001~10 wt % when it is mixed with the liquid type fuel, and thus, can exhibit an excellent effect of improving lubricity with even a small amount thereof, and have excellent storage stability due to anti-oxidation, and thus, can not corrode metals. In addition, the lubricity improver according to the present invention may be used as lube base oil, and preferably, may be mixed with general lube base oil in 0.000001~99 wt %.

DETAILED DESCRIPTION OF EMBODIMENTS

Hereinafter, the present invention will be described in more detail with reference to examples. However, the scope of the present invention is not limited to the examples below.

PREPARATION EXAMPLE 1

Preparation of Compound 1

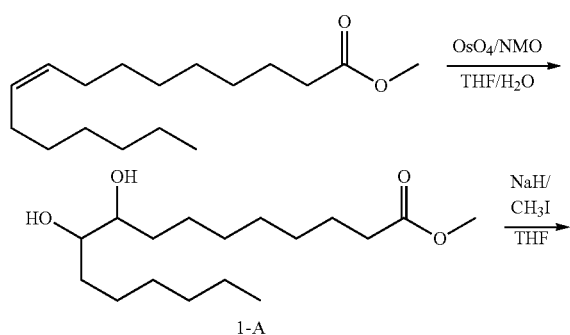

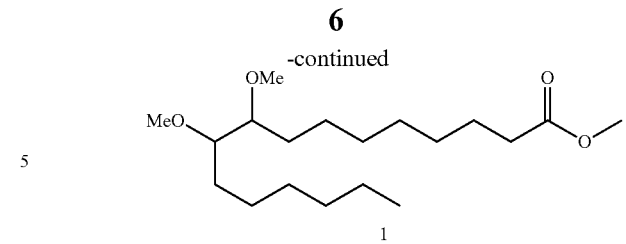

Preparation of Compound 1-A

Methyl palmitoleate (10 g, 1 eq) containing a double bond, as a start material, a mixture solvent of tetrahydrofuran (THF) and water (a volume ratio of THF/$H_2O$=3/1) (80 mL), $OsO_4$ (Osmium tetraoxide, 4% in $H_2O$) (24 mL, 0.1 eq), and NMP (4-Methylmorpholine N-Oxide) (5.65 g, 1.5 eq) were reacted at room temperature for 2 hours. When the reaction was completed, an aqueous $NaHCO_3$ solution (100 mL) was added thereto, and then the organic layer was extracted with ethyl acetate (100 mL× three times), followed by column chromatography, thereby separating and purifying Compound 1-A (9.35 g, yield 83%).

$^1$H-NMR (400 MHz, $CDCl_3$); δ 3.66 (s, 3H), 3.56 (bs, 2H), 3.16 (bs, 2H), 2.30 (t, 2H), 1.62 (t, 2H), 1.51-1.22 (m, 20H), 0.88 (t, 3H)

$^{13}$C-NMR (100 MHz, $CDCl_3$); δ 174.5, 74.9, 74.8, 34.1, 32.0, 31.4, 31.3, 29.6, 29.6, 29.3, 29.2, 26.3, 26.2, 25.0, 22.8, 14.2

Preparation of Compound 1

The purified compound 1-A (9 g, 1 eq) was dissolved in anhydride THF (100 mL), and then NaH (1.71 g, 2.4 eq, 60% in mineral oil) was added thereto at 0° C., followed by addition of $CH_3I$ (10.14 g, 2.4 eq), and then reacted at room temperature for 2 hours. When the reaction has completely ended, water (4 mL) was added thereto, to thereby remove residual NaH. The resultant material was passed through cellite, followed by column chromatography, thereby separating and purifying the target compound 1 (8.95 g, yield: 91%).

$^1$H-NMR (400 MHz, $CDCl_3$); δ 3.66 (s, 3H), 3.40 (s, 6H), 3.38 (bs, 2H), 3.18 (bs, 2H), 2.30 (t, 2H), 1.62-1.23 (m, 18H), 0.89 (t, 3H)

$^{13}$C-NMR (100 MHz, $CDCl_3$); δ 174.3, 83.1, 82.8, 82.8, 74.6, 70.0, 34.2, 32.0, 31.9, 30.4, 29.8, 29.7, 29.5, 29.2, 28.0, 26.2, 25.1, 22.8, 14.2

PREPARATION EXAMPLE 2

Preparation of Compound 2

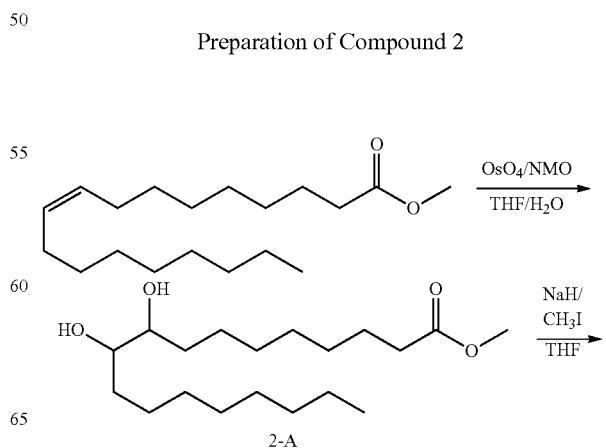

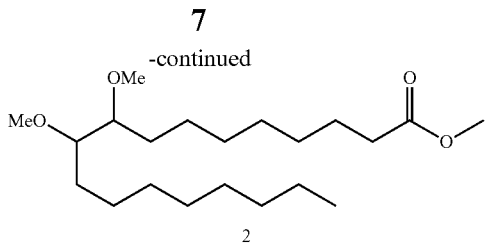

2

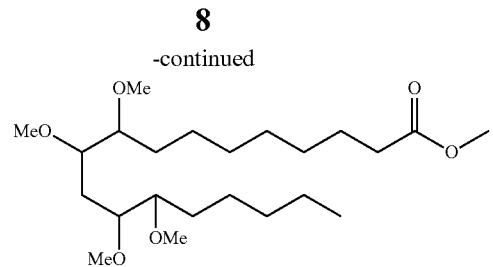

3

Preparation of Compound 2-A

Methyl oleate (10 g, 1 eq) containing a double bond, as a start material, a mixture solvent of tetrahydrofuran (THF) and water (a volume ratio of THF/H$_2$O=3/1) (80 mL), OsO$_4$ (Osmium tetraoxide, 4% in H$_2$O) (21.43 g, 0.1 eq), and NMP (4-Methylmorpholine N-Oxide) (5.12 g, 1.5 eq) were reacted at room temperature for 2 hours. When the reaction was completed, an aqueous NaHCO$_3$ solution (100 mL) was added thereto, and then the organic layer was extracted with ethyl acetate (100 mL× three times), followed by column chromatography, thereby separating and purifying Compound 2-A (9.36 g, yield: 85%).

$^1$H-NMR (400 MHz, CDCl$_3$); δ 3.68 (s, 3H), 3.60 (bs, 2H), 2.30 (t, 2H), 1.83 (t, 2H), 1.62 (t, 2H), 1.51-1.22 (m, 24H), 0.88 (t, 3H)

$^{13}$C-NMR (100 MHz, CDCl$_3$); δ 174.6, 74.9, 74.8, 34.2, 32.1, 31.4, 31.3, 29.9, 29.8, 29.6, 29.5, 29.4, 29.3, 29.2, 26.3, 26.2, 25.0, 22.8, 14.2

Preparation of Compound 2

The compound 2-A (9 g, 1 eq) was dissolved in anhydride THF (100 mL), and then NaH (1.59 g, 2.4 eq) was added thereto at 0° C., followed by addition of CH$_3$I (1.59 g, 2.4 eq, 60% in mineral oil), and then reacted at room temperature for 2 hours. When the reaction was completed ended, water (4 mL) was added thereto, to thereby remove residual NaH. The resultant material was passed through cellite, followed by column chromatography, thereby separating and purifying the target Compound 2 (10.78 g, yield: 92%).

$^1$H-NMR (400 MHz, CDCl$_3$); δ 3.66 (s, 3H), 3.40 (s, 6H), 3.38 (bs, 2H), 3.17 (bs, 2H), 2.30 (q, 2H), 1.62-1.23 (m, 22H), 0.88 (t, 3H)

$^{13}$C-NMR (100 MHz, CDCl$_3$); δ 174.3, 83.2, 83.0, 82.8, 74.6, 70.2, 34.6, 34.3, 32.1, 30.5, 30.5, 30.1, 29.8, 29.7, 29.5, 29.2, 28.0, 26.3, 26.3, 25.2, 22.9, 14.2

PREPARATION EXAMPLE 3

Preparation of Compound 3

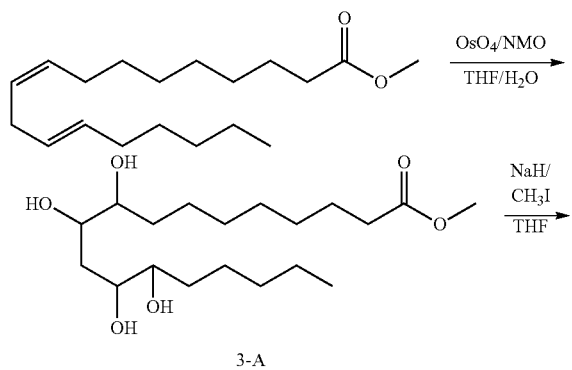

3-A

Preparation of Compound 3-A

Methyl linoleate (10 g, 1 eq) containing a double bond, as a start material, a mixture solvent of tetrahydrofuran (THF) and water (a volume ratio of THF/H$_2$O=3/1) 80 mL), OsO$_4$ (Osmium tetraoxide, 4% in H$_2$O) (43 mL, 0.2 eq), and NMP (4-Methylmorpholine N-Oxide) (10.31 g, 3 eq) were reacted at room temperature for 4 hours. When the reaction was completed, an aqueous NaHCO$_3$ solution (100 mL) was added thereto, and then the organic layer was extracted with ethyl acetate (100 mL× three times), followed by column chromatography, thereby separating and purifying Compound 3-A (9.44 g, yield: 78%).

Preparation of Compound 3

The purified diol compound 3-A (9 g, 1 eq) was dissolved in anhydride THF (200 mL), and then NaH (4.85 g, 4.8 eq, 60% in mineral oil) was added thereto at 0° C., followed by addition of CH$_3$I (17.20 g, 4.8 eq), and then reacted at room temperature for 2 hours. When the reaction has completely ended, water (5 mL) was added thereto, to thereby remove residual NaH. The resultant material was passed through cellite, followed by column chromatography, thereby separating and purifying the target dimethoxy compound 3 (7.73 g, yield: 84%).

PREPARATION EXAMPLE 4

Preparation of Compound 4

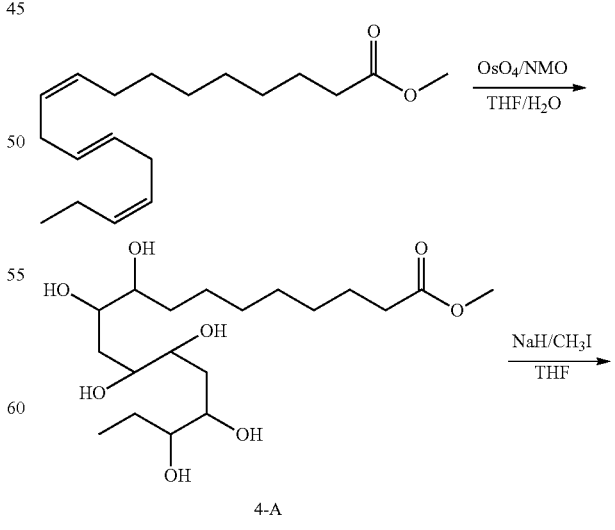

4-A

-continued

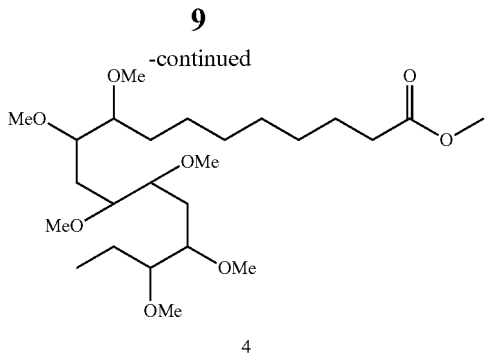

4

Preparation of Compound 4-A

Methyl linoleate (10 g, 1 eq) containing a double bond, as a start material, a mixture solvent of tetrahydrofuran (THF) and water (a volume ratio of THF/H₂O=3/1) 80 mL), OsO₄ (Osmium tetraoxide, 4% in H₂O) (43 mL, 3 eq), and NMP (4-Methylmorpholine N-Oxide) (15.46 g, 4.5 eq) were reacted at room temperature for 2 hours. When the reaction was completed, an aqueous NaHCO₃ solution (100 mL) was added thereto, and then the organic layer was extracted with ethyl acetate (100 mL× three times), followed by column chromatography, thereby separating and purifying Compound 4-A (7.94 g, yield: 64%).

Preparation of Compound 4

The purified diol compound 4-A (7.5 g, 1 eq) was dissolved in anhydride THF (200 mL), and then NaH (6.09 g, 7.2 eq, 60% in mineral oil) was added thereto at 0° C., followed by addition of CH₃I (21.61 g, 7.2 eq), and then reacted at room temperature for 2 hours. When the reaction was completed ended, water (5 mL) was added thereto, to thereby remove residual NaH. The resultant material was passed through cellite, followed by column chromatography, thereby separating and purifying the target dimethoxy compound 4 (5.98 g, yield: 78%).

EXAMPLE 1

Measurement of Oxidation Stability

Oxidation stability was measured on the methoxylated fatty acid methyl ester compounds 1 to 4 prepared in Preparation Examples 1 to 4 by using an oxidation stability tester (743 Rancimat) according to the EN 14112 standard analysis method. Table 1 below shows results obtained by measuring oxidation stability using the oxidation stability tester with respect to the existing biodiesel constituent molecules (start materials of Preparation Examples 1 to 4) and the methoxylated fatty acid methyl ester compounds 1 to 4 prepared in Preparation Examples 1 to 4.

TABLE 1

| Lubricity Improver Composition | | Oxidation Stability (h) |
|---|---|---|
| Preparation Example 1 | Compound 1 | >40 |
| Preparation Example 2 | Compound 2 | >40 |
| Preparation Example 3 | Compound 3 | >40 |
| Preparation Example 4 | Compound 4 | >40 |
| Comparative Example 1 | Methyl palmitoleate | 14.3 |
| Comparative Example 2 | Methyl oleate | 15.1 |
| Comparative Example 3 | Methyl linoleate | 5.8 |
| Comparative Example 4 | Methyl linolenate | 0.4 |

It can be seen from Table 1 above, that oxidation stability (storage stability) of the fatty acid methyl ester derivatives (Compounds 1 to 4) including at least one 1,2-dimethoxy ethylene structural unit obtained by converting a double bond (olefin) of biodiesel into a dimethoxy group was improved.

EXAMPLE 2

Measurement of Lubricity

In order to check lubricity of the lubricity improver compositions including the methoxylated fatty acid methyl ester compounds 1 to 4 prepared in Preparation Examples 1 to 4, a high frequency reciprocating rig (HFRR) by PCS Instrument Company was used, and measurement was carried out according to the ISO 12156 method.

A metal plate (plate having a diameter of 1 cm, by PCS Instrument Company) and a test sphere (metal sphere having an outer diameter of 6 mm, by PCS Instrument Company) were subjected to reciprocating friction while 2 mL of a sample is used, under the conditions of a frequency of 50 Hz and a weight of 200 g, at 60° C. for 75 minutes, and then a mean wear scar diameter (MWSD) generated on the test sphere was measured by using a microscope (Infinity 1 by MEIJI TECHNO Company). Since the generation degree of the mean wear scar diameter is different due to humidity, the humidity in an HFRR analysis cabinet was controlled to be maintained at 30%~50%, which is adopted by the ISO standard method, by using K₂CO₃. The mean wear scar diameter is a trace generated due to friction between the test sphere and the metal plate, and the larger size thereof means that lubricity of the sample is deteriorated. The observed mean wear scar diameter was shown by using a corrected mean wear scar diameter in which humidity and temperature factors are considered at the time of analysis.

Table 2 below shows results obtained by measuring lubricity using the HFRR facilities with respect to the existing biodiesel constituent molecules (start materials of Preparation Examples 1 to 4) and the methoxylated fatty acid methyl ester compounds 1 to 4 prepared in Preparation Examples 1 to 4.

TABLE 2

| Lubricity Improver Composition | | Biodiesel Composition Mean Wear Scar Diameter (μm) |
|---|---|---|
| Preparation Example 1 | Compound 1 | 213 |
| Preparation Example 2 | Compound 2 | 201 |
| Preparation Example 3 | Compound 3 | 153 |
| Preparation Example 4 | Compound 4 | 128 |
| Comparative Example 1 | Methyl palmitoleate | 228 |
| Comparative Example 2 | Methyl oleate | 211 |
| Comparative Example 3 | Methyl linoleate | 175 |
| Comparative Example 4 | Methyl linolenate | 143 |

It can be seen from Table 2 above, that the improvement in lubricity (the decrease in mean wear scar diameter) of the fatty acid methyl ester derivatives (Compounds 1 to 4) including at least one 1,2-dimethoxy ethylene structural unit obtained by converting a double bond (olefin) of biodiesel into a dimethoxy group was observed.

As set forth above, the lubricity improver composition according to the present invention contains a saturated fatty acid methyl ester derivative including at least one 1,2-dimethoxy ethylene structural unit obtained by substituting a double bond (olefin) in the fatty acid methyl ester (FAME), that is easily oxidized and thus have poor storage stability, with a dimethoxy group, and thus, can improve lubricity and storage stability, and reduce friction and wear between two moving faces, to thereby maintain stability and performance of vehicles and machines. Further, the lubricity improver composition of the present invention is ecofriendly since it uses biodiesel obtained from animal and vegetable resources as a start material.

What is claimed is:

1. A lubricity improver comprising a saturated fatty acid methyl ester derivative including at least one structural unit represented by Chemical Formula a below

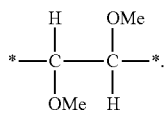

[Formula a]

2. The lubricity improver of claim 1, wherein it includes a methoxylated fatty acid methyl ester derivative represented by Chemical Formula 1 below

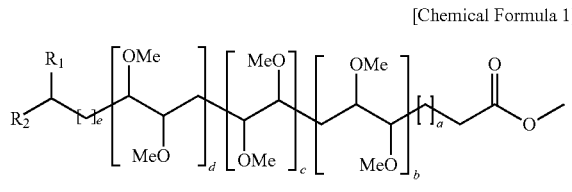

[Chemical Formula 1]

[Wherein Chemical Formula 1, $R_1$ and $R_2$ each are independently hydrogen or

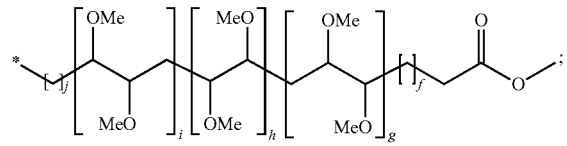

a, e, f, and j each are independently an integer of 1 to 10, and b, c, d, g, h, and i each are independently an integer of 0 to 5, provided that b+c+d and g+h+I each are independently an integer of 1 or greater.]

3. The lubricity improver of claim 2, wherein the methoxylated fatty acid methyl ester derivative of Chemical Formula 1 is prepared by including:
 1) preparing a hydroxylated fatty acid methyl ester derivative of Chemical Formula 3 by hydroxylating biodiesel of Chemical Formula 2 below including at least one double bond; and
 2) preparing the methoxylated fatty acid derivative of Chemical Formula 1 by reacting the hydroxylated fatty acid methyl ester derivative of Chemical Formula 3 with halomethane in the presence of a base

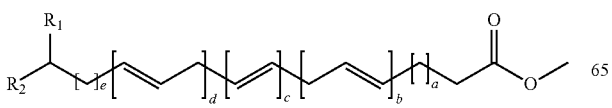

[Chemical Formula 2]

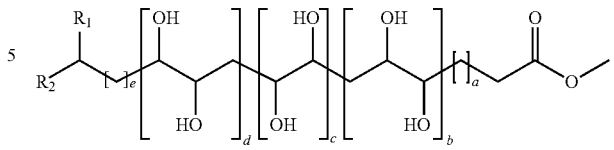

[Chemical Formula 3]

[In Chemical Formulas 2 and 3, $R_1$, $R_2$, a, b, c, d, and e have the same meanings as those defined in claim 2.]

4. The lubricity improver of claim 3, wherein in Stage 1), the hydroxylating is carried out in the presence of an $OsO_4$ catalyst and 4-methylmorpholine N-oxide or t-butyl hydroperoxide.

5. The lubricity improver of claim 3, wherein in Stage 2), the base is selected from NaH, KH, KOt-Bu, NaOBu, and $NaNH_2$.

6. The lubricity improver of claim 2, wherein it includes a methoxylated fatty acid methyl ester derivative represented by Chemical Formula 4 below

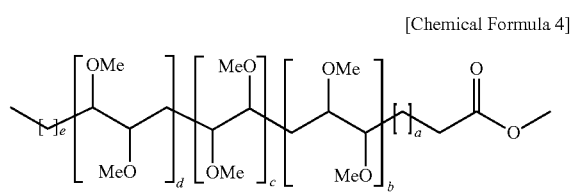

[Chemical Formula 4]

[In Chemical Formula 4, a, b, c, d, and e have the same meanings as those defined in claim 2.]

7. The lubricity improver of claim 6, wherein the methoxylated fatty acid methyl ester derivative is selected from below

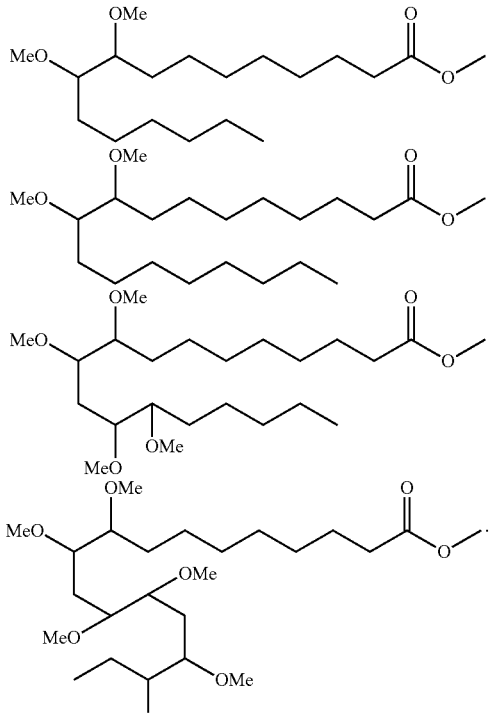

8. The lubricity improver of claim 3 wherein the biodiesel of Chemical Formula 2 is prepared from animal or vegetable oil.

9. The lubricity improver of claim 8, wherein the animal or vegetable oil is selected from fat, pig fat, chicken fat, fish oil, soybean oil, olive oil, rapeseed oil, palm oil, perilla oil, sesame oil, sunflower oil, grape seed oil, red pepper seed oil, jatropha, cottonseed oil, and waste edible-oil.

* * * * *